(12) United States Patent
Kuhn et al.

(10) Patent No.: US 8,320,984 B2
(45) Date of Patent: Nov. 27, 2012

(54) OPTICAL SENSOR FOR MEDICAL DEVICE

(75) Inventors: Jonathan L. Kuhn, Ham Lake, MN (US); Thomas A. Anderson, New Hope, MN (US); Can Cinbis, Shoreview, MN (US); Jeffrey M. Jelen, New Hope, MN (US); Timothy Davis, Coon Rapids, MN (US); James K. Carney, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 440 days.

(21) Appl. No.: 12/765,345

(22) Filed: Apr. 22, 2010

(65) Prior Publication Data

US 2011/0190608 A1 Aug. 4, 2011

Related U.S. Application Data

(60) Provisional application No. 61/299,705, filed on Jan. 29, 2010.

(51) Int. Cl.
*A61B 5/00* (2006.01)

(52) U.S. Cl. ........................................ 600/316

(58) Field of Classification Search .................. 600/316; 396/14–15
See application file for complete search history.

(56) References Cited

U.S. PATENT DOCUMENTS

| | | |
|---|---|---|
| 3,985,449 A | 10/1976 | Patrin |
| 4,100,562 A | 7/1978 | Sugawara et al. |
| 4,202,339 A | 5/1980 | Wirtzfeld et al. |
| 4,467,807 A | 8/1984 | Bornzin |
| 4,730,389 A | 3/1988 | Baudino et al. |
| 5,010,381 A | 4/1991 | Shiba |
| 5,144,381 A | 9/1992 | Furuyama et al. |
| 5,556,421 A | 9/1996 | Prutchi et al. |
| 5,596,987 A * | 1/1997 | Chance ................. 600/310 |

(Continued)

FOREIGN PATENT DOCUMENTS

WO 0025862 A1 5/2000

(Continued)

OTHER PUBLICATIONS

Thomas Jensen et al., "Independent Component Analysis Applied to Pulse Oximetry in the Estimation of the Arterial Oxygen Saturation ($S_pO_2$)—a Comparative Study", $31^{st}$ Annual International Conference of the IEEE EMBS, Minneapolis, Minnesota Sep. 2-6, 2009 (pp. 4039-4044).

(Continued)

*Primary Examiner* — Clayton E LaBalle
*Assistant Examiner* — Dennis Hancock
(74) *Attorney, Agent, or Firm* — Evans M. Mburu; Michael C. Soldner; Stephen W. Bauer

(57) ABSTRACT

An optical sensor for a medical device includes a fixed lens spacing between emit and receive modules to achieve target sensor sensitivity, while varying other sensor parameters in order to increase signal amplitude without increasing power demand. The size of at least one of emit and receive module lenses of an optical sensor, and the offset between the optoelectronic component and the respective lens of at least one of emit and receive modules is decreased to increase amplitude of the signal received by the receive module from the emit module.

30 Claims, 12 Drawing Sheets

U.S. PATENT DOCUMENTS

| | | | |
|---|---|---|---|
| 5,902,326 | A | 5/1999 | Lessar et al. |
| 6,125,290 | A | 9/2000 | Miesel |
| 6,144,866 | A | 11/2000 | Miesel et al. |
| 6,198,952 | B1 | 3/2001 | Miesel |
| 6,356,774 | B1 | 3/2002 | Bernstein et al. |
| 6,409,675 | B1 | 6/2002 | Turcott |
| 6,491,639 | B1 | 12/2002 | Turcott |
| 6,661,167 | B2 | 12/2003 | Eliashevich et al. |
| 6,711,423 | B2 | 3/2004 | Colvin |
| 7,013,178 | B2 | 3/2006 | Reinke et al. |
| 7,152,977 | B2 | 12/2006 | Ruda et al. |
| 7,167,309 | B2 | 1/2007 | Saxena et al. |
| 7,415,298 | B2 | 8/2008 | Casciani et al. |
| 7,961,305 | B2 * | 6/2011 | Xu et al. ............ 356/39 |
| 2004/0176669 | A1 | 9/2004 | Colvin, Jr. |
| 2004/0197267 | A1 | 10/2004 | Black et al. |
| 2004/0220629 | A1 | 11/2004 | Kamath et al. |
| 2004/0246744 | A1 | 12/2004 | Krupa et al. |
| 2005/0006651 | A1 | 1/2005 | LeBoeuf et al. |
| 2006/0255353 | A1 | 11/2006 | Taskar et al. |
| 2007/0203405 | A1 * | 8/2007 | Shimomura ............ 600/316 |
| 2009/0076353 | A1 | 3/2009 | Carpenter et al. |
| 2009/0156905 | A1 | 6/2009 | Ries et al. |
| 2009/0156912 | A1 | 6/2009 | Kuhn et al. |
| 2009/0326346 | A1 | 12/2009 | Kracker et al. |
| 2010/0185262 | A1 | 7/2010 | Kuhn et al. |

FOREIGN PATENT DOCUMENTS

| | | |
|---|---|---|
| WO | 2007/122375 A2 | 11/2007 |
| WO | 2008118042 A1 | 10/2008 |
| WO | 2009/076063 A1 | 6/2009 |
| WO | 2009137426 A1 | 11/2009 |

OTHER PUBLICATIONS

Sune Duun et al., "A Novel Ring Shaped Photodiode for Reflectance Pulse Oximetry in Wireless Applications", IEEE Sensors Conference, 2007 (pp. 596-599).

U.S. Appl. No. 61/146,469, filed Jan. 22, 2009 entitled "Co-Location of Emitters and Detectors and Method of Operation".

U.S. Appl. No. 12/765,434, filed Apr. 22, 2010 entitled "Optical Sensor for Medical Device".

U.S. Appl. No. 12/765,396, filed Apr. 22, 2010 entitled "Optical Sensor for Medical Device".

Mendelson et al. "Design and Evaluation of a New Reflectance Pulse Oximeter Sensor," Medical Instrumentation, Philadelphia, PA, vol. 22, No. 4, Aug. 1, 1988, pp. 167-173.

International Search Report and Written Opinion of international application No. PCT/US2010/032091, dated Oct. 8, 2010, 16 pp.

Reply to Written Opinion dated Oct. 19, 2010, from international application No. PCT/US2010/032096, filed Nov. 28, 2011, 15 pp.

Reply to Written Opinion dated Oct. 8, 2010, from international application No. PCT/US2010/032091, filed Nov. 28, 2011, 18 pp.

Reply to Written Opinion dated Oct. 15, 2010, from international application No. PCT/US2010/032080, filed Nov. 28, 2011, 11 pp.

Written Opinion dated Apr. 10, 2012, from international application No. PCT/US2010/032091, 11 pp.

Written Opinion dated Apr. 10, 2012, from international application No. PCT/US2010/032096, 10 pp.

Written Opinion dated Apr. 10, 2012, from international application No. PCT/US2010/032080, 10 pp.

International Preliminary Report on Patentability from international application No. PCT/US2010/032091, dated Jun. 15, 2012, 28 pp.

International Preliminary Report on Patentability from international application No. PCT/US2010/032096, dated Jun. 15, 2012, 23 pp.

International Preliminary Report on Patentability from international application No. PCT/US2010/032080, dated Jun. 15, 2012, 19 pp.

Kuhn, et al., "Optical Sensor for Medical Device", filed Apr. 22, 2010, U.S. Appl. No. 12/765,396, 36 pages.

Kuhn, et al., "Optical Sensor for Medical Device", filed Apr. 22, 2010, U.S. Appl. No. 12/765,434, 36 pages.

* cited by examiner

OPTICAL SENSOR FOR MEDICAL DEVICE

This application claims the benefit of U.S. Provisional Application No. 61/299,705, filed Jan. 29, 2010, the entire content of which is incorporated herein by this reference.

TECHNICAL FIELD

This disclosure relates to medical devices, and, more particularly, to optical sensors employed in such devices.

BACKGROUND

A variety of implantable medical devices for delivering a therapy and/or monitoring a physiological condition have been clinically implanted or proposed for clinical implantation in patients. Implantable medical devices may deliver electrical stimulation or drug therapy to, and/or monitor conditions associated with, the heart, muscle, nerve, brain, stomach or other organs or tissue, as examples. Some implantable medical devices may employ one or more elongated electrical leads carrying stimulation electrodes, sense electrodes, and/or other sensors. Implantable medical leads may be configured to allow electrodes or other sensors to be positioned at desired locations for delivery of stimulation or sensing. For example, electrodes or sensors may be carried at a distal portion of a lead. A proximal portion of the lead may be coupled to an implantable medical device housing, which may contain circuitry such as stimulation generation and/or sensing circuitry. Other implantable medical devices may employ one or more catheters through which the devices deliver a therapeutic fluid to a target site within a patient.

Implantable medical devices may include one or more physiological sensors, which may be used in conjunction with the device to provide signals related to various physiological conditions from which a patient state or the need for a therapy can be assessed. Examples of such implantable medical devices include heart monitors, pacemakers, implantable cardioverter defibrillators (ICDs), myostimulators, neurostimulators, therapeutic fluid delivery devices, insulin pumps, and glucose monitors.

Optical sensors may be employed in implantable medical devices as physiological sensors configured to detect changes in light modulation by a body fluid or tissue volume caused by a change in a physiological condition in the body fluid or tissue. Such optical sensors can be used, for example, for detecting changes in metabolite levels in the blood, such as oxygen saturation levels or glucose level, or changes in tissue perfusion. Monitoring such physiological conditions provides useful diagnostic measures, and can be used in managing therapies for treating a medical condition. For example, a decrease in blood oxygen saturation or in tissue perfusion may be associated with insufficient cardiac output or respiratory function. Thus monitoring such signals allows an implantable medical device to respond to a decrease in oxygen saturation or tissue perfusion, for example by delivering electrical stimulation therapies to the heart to restore a normal hemodynamic function.

SUMMARY

In general, examples disclosed herein are directed to an optical sensor for a medical device that includes a fixed lens spacing between emit and receive modules to achieve target sensor sensitivity, while varying other sensor parameters in order to increase signal amplitude without increasing power demand.

In one example, a medical device includes a housing and an optical sensor connected to the housing. The optical sensor includes an emit module and a receive module offset laterally from the emit module. The receive module is offset laterally from the emit module. Each of the emit and receive modules comprises a cavity within which an opto-electronic component is arranged and a lens generally defining one end of the cavity offset from the opto-electronic component. A size of the lens of the emit module is less than a size of the lens of the receive module.

In another example, an optical sensor connected to a housing of a medical device includes an emit module and a receive module offset laterally from the emit module. Each of the emit and receive modules include a cavity within which an opto-electronic component is arranged and a lens generally defining one end of the cavity offset from the opto-electronic component. The size of the lens of the emit module is less than the size of the lens of the receive module.

In another example, a method of constructing an optical sensor connected to a housing of a medical device includes providing an emit module and a receive module offset laterally from the emit module. Each of the emit and receive modules includes a cavity within which an opto-electronic component is arranged and a lens generally defining one end of the cavity offset from the opto-electronic component. A size of the lens of the emit module is selected to be less than a size of the lens of the receive module.

The details of one or more examples are set forth in the accompanying drawings and the description below. Other features, objects, and advantages of the disclosure will be apparent from the description and drawings, and from the claims.

DETAILED DESCRIPTION

Figure 1:
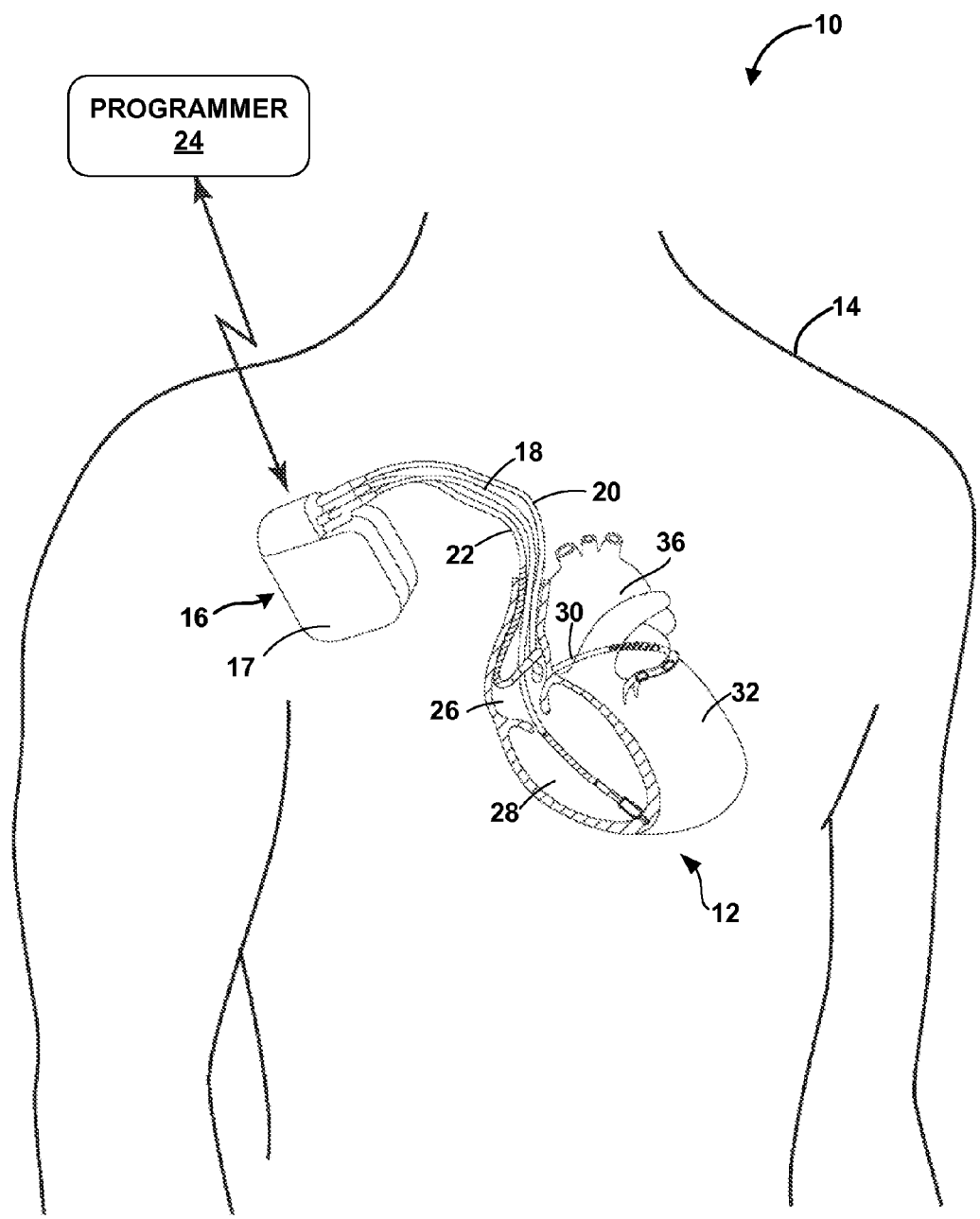
FIG. 1 is a conceptual drawing illustrating an example system that includes an implantable medical device (IMD) coupled to implantable medical leads.

FIG. 1 is a conceptual diagram illustrating an example system 10 that may be used for sensing of physiological parameters of patient 14 and/or to provide therapy to heart 12 of patient 14. Therapy system 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. Patient 14 is ordinarily, but not necessarily, a human patient.

Leads 18, 20, 22 extend into the heart 12 of patient 16 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

System 10 may, in some examples, additionally or alternatively include one or more leads or lead segments (not shown in FIG. 1) that deploy one or more electrodes within the vena cava or other vein. These electrodes may allow alternative electrical sensing configurations that may provide improved or supplemental sensing in some patients. Furthermore, in some examples, therapy system 10 may include temporary or permanent epicardial or subcutaneous leads, instead of or in addition to leads 18, 20 and 22. Such leads may be used for one or more of cardiac sensing, pacing, or cardioversion/defibrillation.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may detect arrhythmia of heart 12, such as tachycardia or fibrillation of ventricles 28 and 32, and may also provide defibrillation therapy and/or cardioversion therapy via electrodes located on at least one of the leads 18, 20, 22. In some examples, IMD 16 may be programmed to deliver a progression of therapies, e.g., pulses with increasing energy levels, until a fibrillation of heart 12 is stopped. IMD 16 detects fibrillation employing any of a number of known fibrillation detection techniques.

In addition to employing electrodes connected to one of the leads 18, 20, 22 and/or the housing of IMD 16 to sense the physiological state of patient 14, IMD 16 includes at least one optical sensor that may be configured to detect changes in light modulation by a body fluid or tissue volume of the patient caused by a change in a physiological condition in the body fluid or tissue. For example, the optical sensor(s) of IMD 16 may be employed to detect changes in metabolite levels in the blood of patient 14 including, e.g., oxygen saturation levels or glucose level, or changes in tissue perfusion. IMD 16 may employ the optical sensor(s) to monitor physiological conditions of patient 14 for diagnostic purposes and/or to manage therapy delivered to the patient. For example, a decrease in blood oxygen saturation or in tissue perfusion may be associated with insufficient cardiac output or respiratory function. By monitoring these physiological parameters IMD 16 may, for example, respond to a decrease in oxygen saturation or tissue perfusion by delivering electrical stimulation via one or more of leads 18, 20, and 22 to heart 12 of patient 14 to restore normal hemodynamic function.

Programmer 24 shown in FIG. 1 may be a handheld computing device, computer workstation, or networked computing device. Programmer 24 may include a user interface that receives input from a user. The user interface may include, for example, a keypad and a display, which may for example, be a cathode ray tube (CRT) display, a liquid crystal display (LCD), an organic or standard light emitting diode (OLED/LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display. In some examples, the user may also interact with programmer 24 remotely via a networked computing device.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16 that was obtained based on signals received from the optical sensors of the device. A user may also interact with programmer 24 to program IMD 16, e.g., to select values for operational parameters of the IMD.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. The user may also employ programmer 24 to retrieve information from IMD 16 regarding physiological parameters of patient 14 detected by the optical sensor(s) of the device including, e.g., blood oxygen saturation and tissue perfusion. As another example, the user may use programmer 24 to retrieve information from IMD 16 regarding the performance or integrity of IMD 16 or other components of system 10, such as leads 18, 20 and 22, or a power source of IMD 16. In some examples, this information may be presented to the user as an alert.

The user may use programmer 24 to program a therapy progression, select electrodes used to deliver defibrillation pulses, select waveforms for the defibrillation pulse, or select or configure a fibrillation detection algorithm for IMD 16. The user may also use programmer 24 to program aspects of other therapies provided by IMD 16, such as cardioversion or pacing therapies. IMD 16 and programmer 24 may communicate via wireless communication using any number of known techniques.

Figure 2:
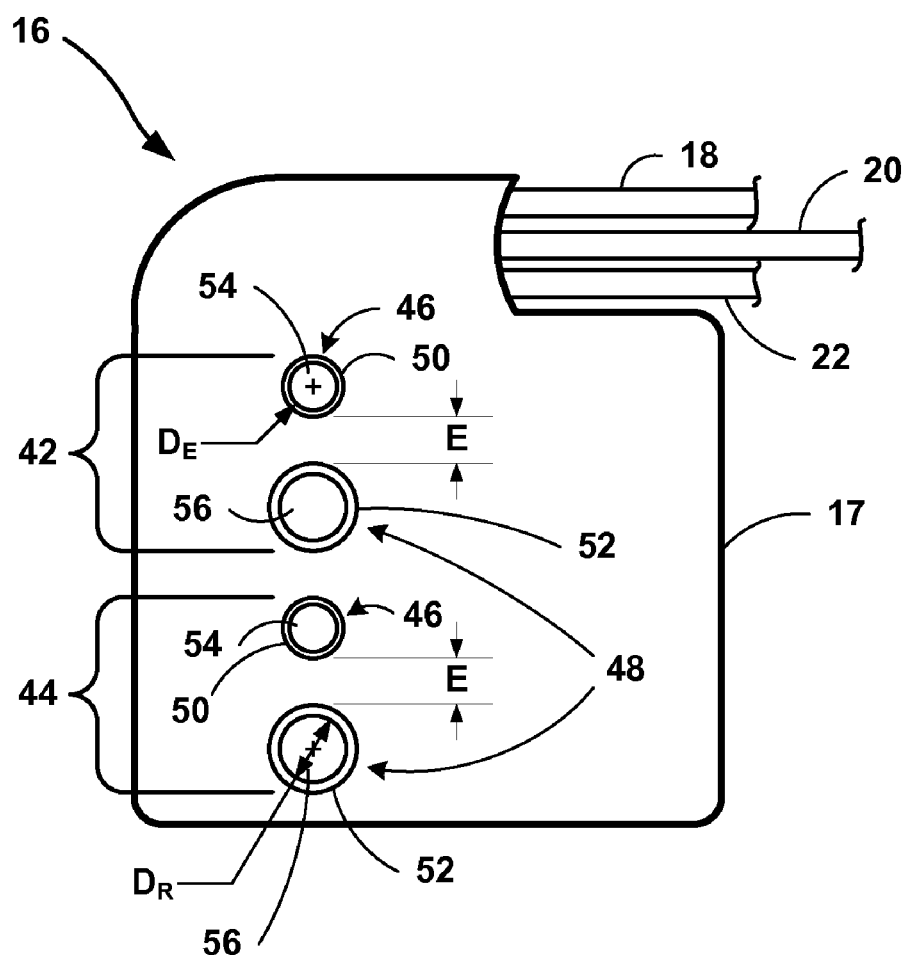
FIG. 2 is a conceptual drawing illustrating the example IMD of FIG. 1 including a number of optical sensor modules.

FIG. 2 is a conceptual diagram illustrating IMD 16 including optical sensors 42 and 44, each of which include emit module 46 and receive module 48 laterally offset from one another. While, generally speaking, emit module 46 of sensor 42 emits optical signals to receive module 48 of sensor 42 and emit module 46 of sensor 44 emits optical signals to receive module 48 of sensor 44, examples according to this disclosure include emit module 46 of sensor 42 emitting optical signals to receive module 48 of sensor 44, as well as other emit and receive module combinations of sensors 42 and 44. Furthermore, although IMD 16 of FIG. 2 includes two optical sensors 42, 44, other example devices may include fewer or more optical sensors. Finally, as described in greater detail with reference to FIG. 9, optical sensors employed in therapy system 10 of FIG. 1, or other medical systems, may be positioned in locations other than connected to IMD 16. For example, optical sensors 42, 44 may be connected to one or more of leads 18, 20, or 22. In another example, optical sensors may be located in a separate device that communicates via telemetry with IMD 16 or communicates via telemetry or wire with Programmer 24.

Referring again to FIG. 2, each of emit and receive module 46, 48 include an opto-electronic component (not shown) arranged within a cavity in housing 17 of IMD 16. The cavity is generally defined by a circuit board (not shown), a side wall (not shown) protruding from the circuit board and surrounding the opto-electronic component, a lens offset from the circuit board, and a ferrule (50 or 52 for emit and receive modules 46, 48 respectively) connected to housing 17 of IMD 16, the lens and the side wall (not shown). As used herein, the term "opto-electronic component" refers to any electrical circuit component capable of emitting light in response to an applied voltage or current or emitting current or changing an inherent physical property in response to exposure to light, including, e.g., light emitting diodes (LEDs), vertical cavity surface emitting lasers (VCSELs), photoresistors or light dependent resistors, photodiodes, phototransistors, photovoltaic cells, or charge-coupled devices.

In order to detect changes in a physiological condition of patient 14, the opto-electronic component of one of the emit modules 46 emits an optical signal out of transparent lens 54 into adjacent body fluid or tissue volume of the patient. The optical signal from emit module 46 interacts with the adjacent body fluid or tissue volume of patient 14, after which a portion of the optical signal modulated by the body fluid or tissue volume of patient 14 is reflected off of the fluid or volume through lens 56 of one of receive modules 48. The optical signal received by receive module 48 is detected by the opto-electronic component of the receive module. The modulation of the optical signal received by receive module 48 from emit module 46 may be interpreted by IMD 16 to detect a physiological condition of patient 14, e.g. to detect blood oxygen saturation or tissue perfusion of the patient. Employing sensors 42, 44, IMD 16 may, for example, respond to decreases in oxygen saturation or tissue perfusion by delivering electrical stimulation via one or more of leads 18, 20, and 22 to heart 12 of patient 14 to restore normal hemodynamic function. Optical sensors 42, 44 may be operated continuously at a relatively low duty cycle, or the sensors may be triggered by other sensor signals including, e.g., electrocardiogram (ECG) information for patient 14 produced by electrodes connected to one or more of leads 18, 20, 22 and/or housing 17 of IMD 16 that signals an episode of interest.

Generally speaking, increasing distance between emit and receive lenses 54, 56 of emit and receive modules 46, 48 respectively increases sensitivity, thereby increasing the granularity of physiological change each of sensors 42, 44 is capable of detecting and improving the limits within which signals from the emit module are detectable by receive module. Although the precise relationship between lens distance and sensor sensitivity may not be known, empirical data gathered from a study of an implantable medical device including optical sensors similar to those described in this disclosure showed that 10 millimeter center-to-center lens spacing provides substantially improved sensitivity over 7 millimeters in sensors with emit and receive modules including approximately 2.5 millimeter diameter windows. However, the amplitude of the optical signal that reaches the opto-electronic component of the receive module decreases exponentially as lens spacing is increased. Although signal amplitude may be increased by increasing power to the emit module of the optical sensor, such increased power demand disadvantageously decreases device longevity and increases detection times by decreasing the thermal stability of the sensor.

In view of the foregoing relationships between sensor configuration and performance, the examples described in this disclosure are directed to techniques for improving optical sensor signal amplitude for a target sensor sensitivity. Lens spacing is one of the most significant controlling parameters for optical signal body fluid or tissue interaction, i.e. optical sensor sensitivity. As such, the disclosed techniques fix lens spacing to achieve target sensor sensitivity, while varying other sensor parameters in order to increase signal amplitude without increasing power demand. In particular, the disclosed examples select the size, $D_E$ and $D_R$ of emit and receive lenses 54, 56 respectively in FIG. 2, and the offset between each of lenses 54, 56, and the respective opto-electronic components of each of emit and receive modules 46, 48 to increase the amplitude of the signal that is received by the receive module of an optical sensor from the emit module. Additionally, in some examples, the arrangement of the opto-electronic component within the receive module is improved by masking the receive module lens with an opaque member to create a masked lens leading edge that is aligned with a leading edge of the opto-electronic component and that acts to effectively increase the edge-to-edge lens spacing between the emit and receive modules.

Masking receive lens 56 may improve the sensitivity of the light receiving opto-electronic component versus lens spacing, e.g. edge-to-edge distance. Without the mask, due to the exponential decay of light versus distance from the light emitting opto-electronic component to the light receiving opto-electronic component, a disproportionately large amount of the signal produced by the light receiving opto-electronic component comes from the "leading edge" of receive lens 56 nearest to emit lens 54. As you move away from this leading edge or point on receive lens 56, the signal quality is improved, but the amplitude decays exponentially. By masking lens 56 of receive module 48 the light emitted by emit module 46 and received by the receive module is more uniformly distributed across the light receiving opto-electronic component of the receive module.

In this disclosure, spacing between emit and receive lenses 54, 56 is generally expressed as edge-to-edge lens distance, E, as shown in FIG. 2. However, lens spacing may, in other examples, be expressed as other distances including, e.g., center-to-center lens spacing in optical sensors employing circular windows.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12. As noted above, in some examples, IMD 16 may be implanted along with a separate sensor device that includes optical sensors 42, 44 communicatively connected to the IMD. Such a separate sensor device may be either implanted at the same or a different site from IMD 12 or may be external to patient 14.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. Other example therapy systems may include a single lead that extends from IMD 16 into right atrium 26 or right ventricle 28, or two leads that extend into a respective one of the right ventricle 26 and right atrium 26. Additionally, in examples in which IMD 16 or a separate sensor device including sensors 42, 44 is employed for integrated diagnostic applications, there may be no external leads or other therapeutic components.

Although optical sensing techniques according to this disclosure are described in the context of devices including cardiac stimulation and/or sensing leads, the examples disclosed herein may also be employed in other types of implantable medical devices including, e.g., myostimulators, neurostimulators, therapeutic fluid delivery devices, insulin pumps, and glucose monitors.

Figure 3:
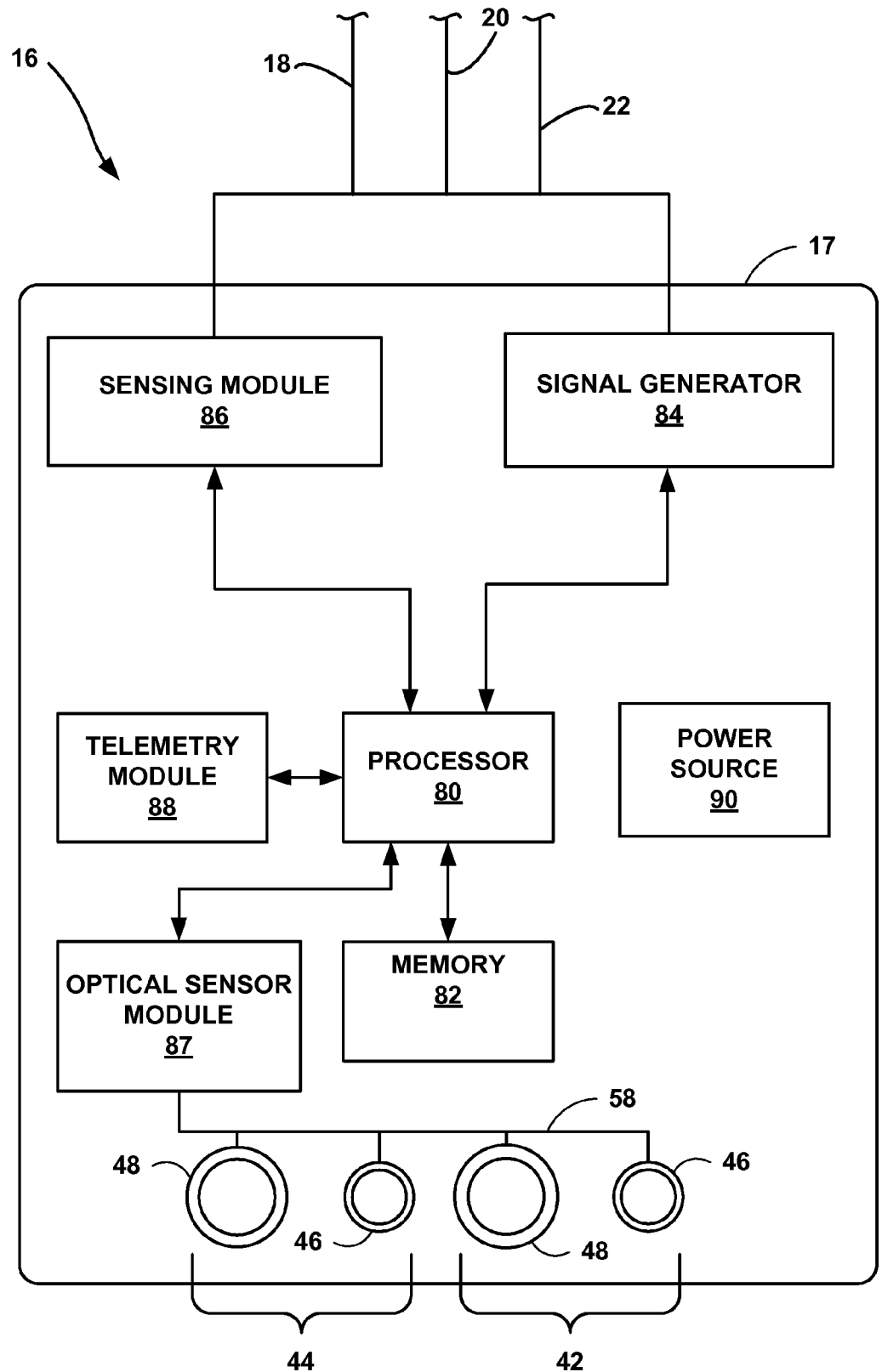
FIG. 3 is a functional block diagram illustrating an example configuration of the IMD of FIG. 1.

FIG. 3 is a functional block diagram illustrating an example configuration of IMD 16. In the illustrated example, IMD 16 includes a processor 80, memory 82, signal generator 84, electrical sensing module 86, optical sensor module 87, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver stimulation therapy to heart 12 according to one or more of therapy programs, which may be stored in memory 82. For example, processor 80 may control signal generator 84 to deliver electrical pulses with the amplitudes, pulse widths, frequency, or electrode polarities specified by a therapy program stored in memory 82.

Signal generator 84 is electrically coupled to electrodes via conductors of the respective lead 18, 20, 22, or, in the case of a housing electrode connected to housing 17 of IMD 16, via an electrical conductor disposed within the housing. Signal generator 84 is configured to generate and deliver electrical stimulation therapy to heart 12. For example, signal generator 84 may deliver defibrillation shocks as therapy to heart 12 via at least two electrodes connected to one or more of leads 18, 20, and 22. Signal generator 84 may also deliver pacing pulses via, e.g. ring or helical electrodes coupled to leads 18, 20, and 22. In some examples, signal generator 84 delivers pacing, cardioversion, or defibrillation stimulation in the form of electrical pulses. In other examples, signal generator may deliver one or more of these types of stimulation in the form of other signals, such as sine waves, square waves, or other substantially continuous time signals.

Signal generator 84 may include a switch module, and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Electrical sensing module 86 monitors signals from at least one electrode connected to one of leads 18, 20, or 22 in order to monitor electrical activity of heart 12 of patient 14. Electrical sensing module 86 may also include a switch module to select which of the available electrodes are used to sense the heart activity. In some examples, processor 80 selects the electrodes that function as sense electrodes, or the sensing configuration, via the switch module within electrical sensing module 86, e.g., by providing signals via a data/address bus.

In some examples, electrical sensing module 86 includes multiple detection channels, each of which comprise an amplifier. Each sensing channel detects electrical activity in respective chambers of heart 12, and may be configured to detect either R-waves or P-waves. In some examples, electrical sensing module 86 or processor 80 includes an analog-to-digital converter for digitizing the signal received from a sensing channel for electrogram signal processing by processor 80. In response to the signals from processor 80, the switch module within electrical sensing module 86 couples the outputs from the selected electrodes to one of the detection channels or the analog-to-digital converter.

Processor 80 may maintain escape interval counters using electrical sensing module 86. Signal generator 84 may include pacer output circuits that are coupled, e.g., selectively by a switching module, to any combination of electrodes connected to leads 18, 20, and 22 appropriate for delivery of a bipolar or unipolar pacing pulse to one or more of the chambers of heart 12. Processor 80 may control signal generator 84 to deliver a pacing pulse to a chamber upon expiration of an escape interval. Processor 80 may reset the escape interval counters upon the generation of pacing pulses by stimulation generator 84, or detection of an intrinsic depolarization in a chamber, and thereby control the basic timing of cardiac pacing functions. The escape interval counters may include P-P, V-V, RV-LV, A-V, A-RV, or A-LV interval counters, as examples. The value of the count present in the escape interval counters when reset by sensed R-waves and P-waves may be used by processor 80 to measure the durations of R-R intervals, P-P intervals, P-R intervals and R-P intervals. Processor 80 may use the count in the interval counters to detect a tachyarrhythmia event, such as an atrial or ventricular fibrillation or tachycardia and/or detect a heart rate, such as an atrial rate or ventricular rate.

Processor 80 may also derive other physiological parameters from signals sensed via electrical sensing module 86. For example, processor 80 may establish one or more indicators of ejection fraction and/or heart failure status from electrical signals sensed via electrical sensing module 86. In particular, impedance signals may be used to determine flow or pressure, which may indicate ejection fraction and/or heart failure status.

IMD 16 also includes optical sensor module 87, which is coupled to optical sensors 42 and 44. Optical sensor module 87 may include a variety of analog and/or digital circuitry configured to drive and process signals of optical sensors 42 and 44. Generally speaking, optical sensor module 87 may include an application specific integrated circuit (ASIC), an electronic circuit, a processor (shared, dedicated, or group) and memory that execute one or more software or firmware programs, a combinational logic circuit, or other suitable components that provide the described functionality. In some examples, optical sensor module 87 includes a sensor driver circuit and sensor processor circuit. Conductor elements 58 extending from optical sensors 42, 44, which may correspond to any of the sensor examples described herein or variations thereof, provide connection to the sensor driver circuit and sensor processor circuit of optical sensor module 87 via any necessary connector elements including, e.g., feedthroughs. The sensor driver circuit provides operational power for optical sensors 42, 44 from power source 90 and controls the timing of sensor operation. Sensor processor circuit receives optical sensor signal output and processes the signal output to estimate a change in a physiological condition, such as blood oxygen saturation, glucose saturation, tissue perfusion or any other physiological condition causing alterations in light modulation by the measurement body fluid or tissue volume.

In other examples, the functions attributed to optical sensor module 87 herein may be executed by other components of IMD 16 including, e.g., processor 80 and memory 82.

In some examples, IMD 16 may also include one or more sensors in addition to optical sensors 42, 44 and separate from the electrodes connected to leads 18, 20, and 22. Processor 80 may monitor a variety of physiological parameters of patient 14 that are relevant to delivering efficacious therapy to the patient via signals generated by such additional sensors. Example sensors include an intracardiac or intravascular pressure sensor, as well as an accelerometer or other sensor capable of detecting heart or blood sounds or vibrations, or patient motion, activity, or posture. Optical sensors 42, 44, as well as any other sensors employed in conjunction with IMD 16, may also be arranged in a device separate from the IMD, which may, in some examples include processor, memory, and/or telemetry modules for processing and communicating signals generated by the sensors.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., electrocardiogram signals) produced by atrial and ventricular sense amp circuits within electrical sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac events that electrical sensing module 86 detects, and transmit the marker codes to programmer 24. In some examples, processor 80 may also retrieve data based on optical signals generated by optical sensor module 87 and transmit the data to programmer 24 in order to, e.g., display changes in a physiological condition of patient 14 including, e.g., blood oxygen saturation, glucose saturation, tissue perfusion or any other physiological condition causing alterations in light modulation via body fluid or tissue volume interaction.

The various components of IMD 16 are coupled to power source 90, which may include a rechargeable or non-rechargeable battery. A non-rechargeable battery may be capable of holding a charge for several years, while a rechargeable battery may be inductively charged from an external device, e.g., on a daily or weekly basis.

Figure 4:
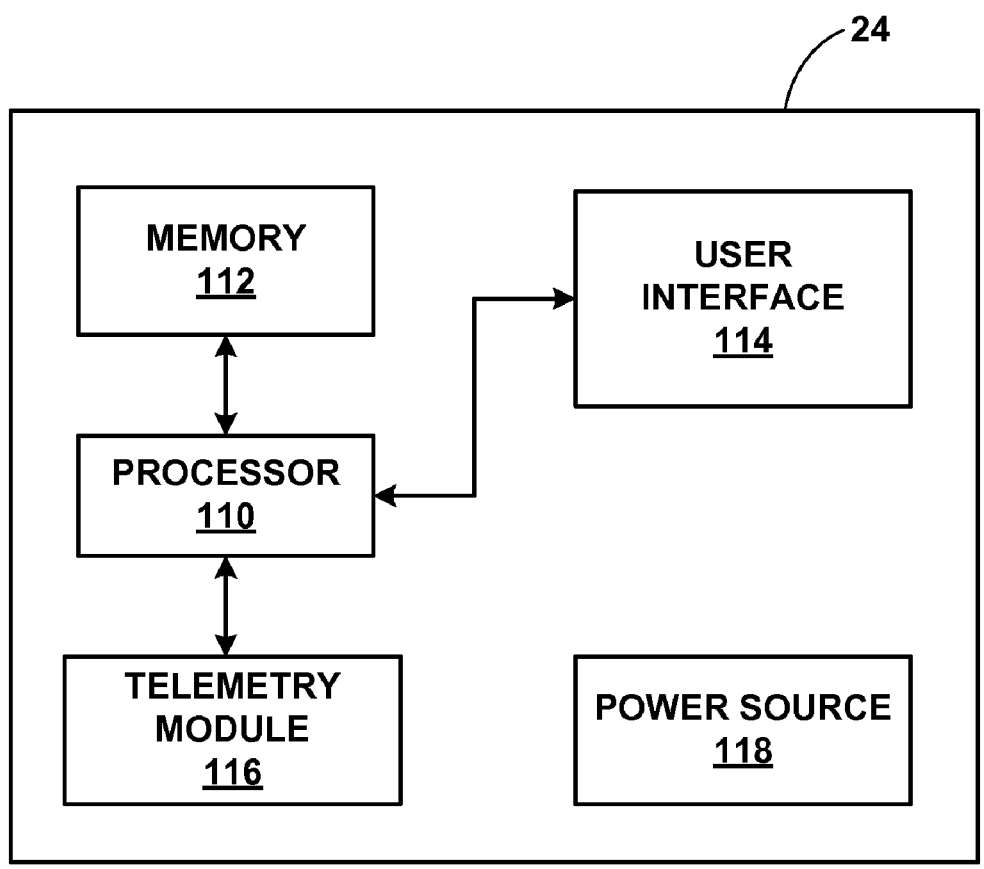
FIG. 4 is a functional block diagram illustrating an example configuration of an external programmer that facilitates user communication with the IMD.

FIG. 4 is a functional block diagram illustrating an example configuration of programmer 24. As shown in FIG. 4, programmer 24 may include a processor 110, memory 112, user interface 114, telemetry module 116, and power source 118. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 114, which may include a display to present a graphical user interface to a user, and a keypad or another mechanism for receiving input from a user.

Processor 110 can take the form of one or more microprocessors, DSPs, ASICs, FPGAs, programmable logic circuitry, or the like, and the functions attributed to processor 110 herein may be embodied as hardware, firmware, software or any combination thereof. Memory 112 may store instructions that cause processor 110 to provide the functionality ascribed to programmer 24 herein, and information used by processor 110 to provide the functionality ascribed to programmer 24 herein. Memory 112 may include any fixed or removable magnetic, optical, or electrical media, such as RAM, ROM, CD-ROM, hard or floppy magnetic disks, EEPROM, or the like. Memory 112 may also include a removable memory portion that may be used to provide memory updates or increases in memory capacities. A removable memory may also allow patient data to be easily transferred to another computing device, or to be removed before programmer 24 is used to program therapy for another patient.

Programmer 24 may communicate wirelessly with IMD 16, such as using RF communication or proximal inductive interaction. This wireless communication is possible through the use of telemetry module 116, which may be coupled to an internal antenna or an external antenna. An external antenna that is coupled to programmer 24 may correspond to the programming head that may be placed over heart 12, as described above with reference to FIG. 1. Telemetry module 116 may be similar to telemetry module 88 of IMD 16 (FIG. 3).

Telemetry module 116 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

Power source 118 delivers operating power to the components of programmer 24. Power source 118 may include a battery and a power generation circuit to produce the operating power. In some examples, the battery may be rechargeable to allow extended operation. Recharging may be accomplished by electrically coupling power source 118 to a cradle or plug that is connected to an alternating current (AC) outlet.

In addition or alternatively, recharging may be accomplished through proximal inductive interaction between an external charger and an inductive charging coil within programmer 24. In other examples, traditional batteries (e.g., nickel cadmium or lithium ion batteries) may be used. In addition, programmer 24 may be directly coupled to an alternating current outlet to power programmer 24. Power source 118 may include circuitry to monitor power remaining within a battery. In this manner, user interface 114 may provide a current battery level indicator or low battery level indicator when the battery needs to be replaced or recharged. In some cases, power source 118 may be capable of estimating the remaining time of operation using the current battery.

Figure 5:
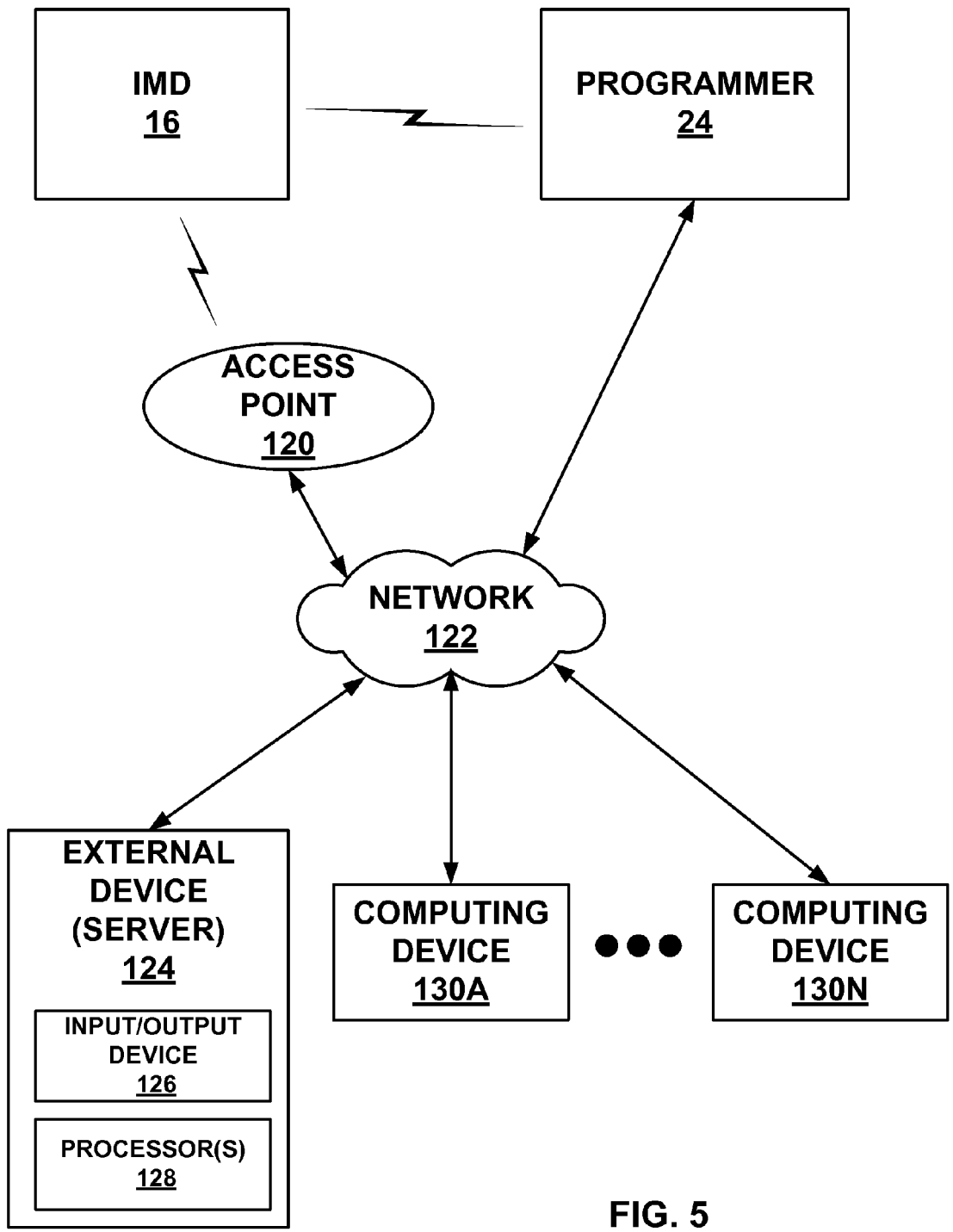
FIG. 5 is a block diagram illustrating an example system that includes an external device, such as a server, and one or more computing devices that are coupled to the IMD and programmer shown in FIG. 1 via a network.

FIG. 5 is a block diagram illustrating an example system that includes an external device, such as a server 124, and one or more computing devices 130A-130N, that are coupled to the IMD 16 and programmer 24 shown in FIG. 1 via a network 122. In this example, IMD 16 may use its telemetry module 88 to communicate with programmer 24 via a first wireless connection, and to communication with an access point 120 via a second wireless connection. In the example of FIG. 5, access point 120, programmer 24, server 124, and computing devices 130A-130N are interconnected, and able to communicate with each other, through network 122. In some cases, one or more of access point 120, programmer 24, server 124, and computing devices 130A-130N may be coupled to network 122 through one or more wireless connections. IMD 16, programmer 24, server 124, and computing devices 130A-130N may each comprise one or more processors, such as one or more microprocessors, DSPs, ASICs, FPGAs, programmable logic circuitry, or the like, that may perform various functions and operations, such as those described herein.

Access point 120 may comprise a device that connects to network 122 via any of a variety of connections, such as telephone dial-up, digital subscriber line (DSL), or cable modem connections. In other examples, access point 120 may be coupled to network 122 through different forms of connections, including wired or wireless connections. In some examples, access point 120 may be co-located with patient 14 and may comprise one or more programming units and/or computing devices (e.g., one or more monitoring units) that may perform various functions and operations described herein. For example, access point 120 may include a home-monitoring unit that is co-located with patient 14 and that may monitor the activity of IMD 16.

In some examples, server 124 or computing devices 130 may perform any of the various functions or operations described herein. As shown in FIG. 5, server 124 may include an input/output device 126 and processors 128, similar to programmer 24. A user may interact with server 124 via input/output device 126, similar to programmer 24. In addition, processors 128 may perform any calculations, data processing, communication relay, or any other task required to treat or monitor patient 14.

Network 122 may comprise a local area network, wide area network, or global network, such as the Internet. In some cases, programmer 24 or server 124 may assemble sensing integrity information in web pages or other documents for viewing by and trained professionals, such as clinicians, via viewing terminals associated with computing devices 130A-130N. The system of FIG. 5 may be implemented, in some aspects, with general network technology and functionality similar to that provided by the Medtronic CareLink® Network developed by Medtronic, Inc., of Minneapolis, Minn.

Figure 6A:
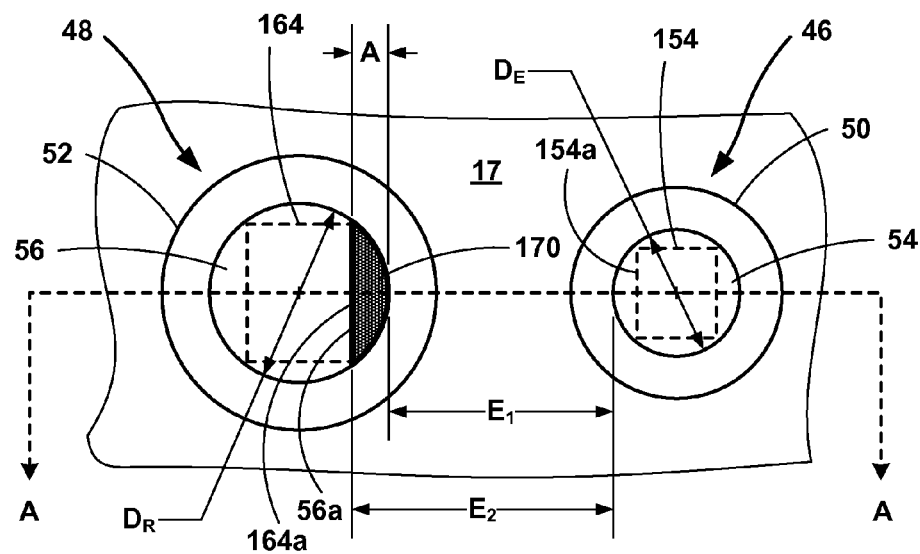
FIGS. 6A and 6B are conceptual drawings respectively illustrating a top view and a cross-sectional view of an example optical sensor.
Figure 6B:
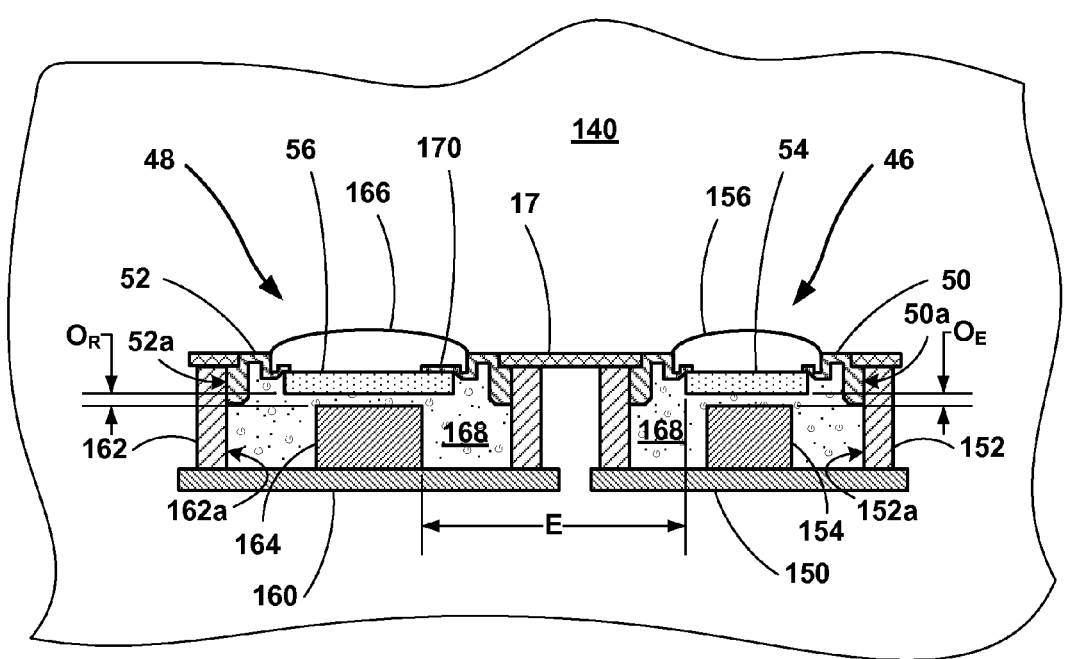

FIGS. 6A and 6B are schematic illustrations of optical sensor 42 including emit module 46 and receive module 48 offset laterally from the emit module. Optical sensor 42 illustrated in FIGS. 6A and 6B may correspond to either of the optical sensors illustrated in FIGS. 2 and 3. FIG. 6A is a plan view of optical sensor 42 including emit module 46 and receive module 48 offset laterally from the emit module. FIG. 6B is a section view of emit module 46 and receive module 48 cut along section line A-A of FIG. 6A.

Emit module 46 includes circuit board 150, side wall 152, light emitting opto-electronic component 154, lens 54, and ferrule 50. Side wall 152 protrudes from circuit board 150 and surrounds light emitting opto-electronic component 154. Lens 54 is offset from circuit board 150. Ferrule 50 is connected to housing 17 of IMD 16, lens 54, and side wall 152.

Side wall 152 surrounds light emitting opto-electronic component 154 to prevent scattering of light and promote transmission of light through lens 54 toward adjacent body fluid or tissue volume 140. Body fluid or tissue volume 140 may correspond to any bodily fluid, such as blood, or body tissue, such as skeletal muscle, neural tissue, myocardium, or the like. Side wall 152 may be formed from a rigid, light-insulating material, including, e.g., a liquid crystal polymer or a metal. In some examples, side wall 152 may be formed from other light-insulating materials including, e.g., any polymer material formed as a molded component, and, in other examples, wall 152 may be formed of a non-rigid material. Side wall 152 is securely coupled to circuit board 150 by, e.g., applying a coating as a hard, die coat dam to hold the wall to the board. In order to increase transmission of light through lens 54 toward adjacent body fluid or tissue volume 140, circuit board 150 and/or side wall 152 may be formed from or coated with a highly reflective material.

Light emitting opto-electronic component 154 may be any electrical circuit component capable of emitting light in response to an applied voltage or current, including, e.g., LEDs and VCSELs. Light emitting opto-electronic component 154 is mounted on circuit board 150 to enable the necessary connections for applying a voltage or current to cause device 154 to emit light. Light emitting component 154 may emit light corresponding to different wavelengths or colors. In one example, in which the sensor including emit module 46 is used for sensing blood oxygen saturation, light emitting opto-electronic component 154 may emit red light (660 nanometer wavelength) or infrared light (890 nanometer wavelength). In another example, in which the sensor including emit module 46 is used for sensing tissue perfusion, light emitting component 154 may emit near-infrared light (800 nanometer wavelength).

In some examples, light emitting opto-electronic component 154 may include multiple light emitting components, e.g. a number of LEDs to emit light of multiple colors and wavelengths. In one such example, one LED of light emitting opto-electronic component 154 may emit red light (660 nanometer wavelength) and another LED of light emitting opto-electronic component 154 may emit infrared light (890 nanometer wavelength). The number of LEDs or other opto-electronic light sources and corresponding light emission wavelengths employed in device 154 may be selected according to the requirements of a particular application and may also depend on the physiological condition being monitored.

Receive module 48 includes circuit board 160, side wall 162, light receiving opto-electronic component 164, lens 56, and ferrule 52. Side wall 162 protrudes from circuit board 160 and surrounds light receiving opto-electronic component 164. Lens 56 is offset from circuit board 160. Ferrule 52 is connected to housing 17 of IMD 16, lens 56, and side wall 162. Light receiving opto-electronic component 164 may be any electrical circuit component capable of generating current or changing a physical property in response to exposure to light, including, e.g., photoresistors or light dependent resistors, photodiodes, phototransistors, photovoltaic cells, or charge-coupled devices.

Side wall 162 surrounds light receiving opto-electronic component 164 to promote transmission of light from adjacent body fluid or tissue volume 140 through lens 56 toward the light receiving component of receive module 48. Side wall 162 may be formed from a rigid, light-insulating material, including, e.g., a liquid crystal polymer or a metal. In some examples, side wall 162 may be formed from other light-insulating materials including, e.g., any polymer material formed as a molded component, and, in other examples, wall 162 may be formed of a non-rigid material. Side wall 162 is securely coupled to circuit board 160 by, e.g., applying a coating as a hard, die coat dam to hold the wall to the board. In order to increase transmission of light through lens 56 toward light receiving opto-electronic component 164, circuit board 160 and/or side wall 162 may be formed from or coated with a highly reflective material. Additionally, in some examples, side wall 162 of receive module 48 may share a common portion with side wall 152 of emit module 46.

Light receiving opto-electronic component 164 may be any electrical circuit component capable of generating current or changing a physical property in response to exposure to light, including, e.g., photoresistors or light dependent resistors, photodiodes, phototransistors, photovoltaic cells, or charge-coupled devices. In some examples, light receive component 164 may include more than one light receiving component. In one example, light receiving opto-electronic component 164 is embodied as an LED formed from a direct band-gap semiconductor that emits narrow spectrum light when electrically biased in the forward direction of the p-n junction. Instead of biasing the LED of light receiving component 164 to emit light, the LED is biased to generate current upon exposure to light, allowing it to function as a light detector. However, in other examples, light receiving opto-electronic component 164 is embodied as another type of light detector including, e.g. a photodiode.

Although example emit and receive modules 46, 48 of FIGS. 6A and 6B include separate circuit boards 150, 160, respectively, in other examples, a single circuit board may be employed that spans both emit and receive modules.

The opto-electronic components of light emitting component 154 and light receiving component 164 may be selected such that one light-detecting component of device 164 is sensitive to the same color of light emitted by one light-emitting component of device 154. In one example, in which a sensor including emit and receive modules 46, 48 is used for sensing blood oxygen saturation, as described above, light emitting opto-electronic component 154 is configured to emit and light receiving opto-electronic component 164 is configured to detect red light (660 nanometer wavelength) or light emitting component 154 is configured to emit and light receiving component 164 is configured to detect infrared light (890 nanometer wavelength). In another example, in which a sensor is used for sensing tissue perfusion, light emitting opto-electronic component 154 is configured to emit and light receiving opto-electronic component 164 is configured to detect near-infrared light (800 nanometer wavelength).

In some examples, one or both of emit module 46 and receive module 48 may include index matching material 168 filling some or all of the cavity of each of the modules in which light emitting opto-electronic component 154 and light receiving opto-electronic component 164 are respectively arranged. Index matching material 168 may be configured with a high refractive index, also referred to herein as "index of refraction", for optically coupling light emitting opto-electronic component 154 and light receiving opto-electronic component 164 with lenses 54 and 56 respectively. Employing index matching material 168 to optically couple light emitting opto-electronic component 154 with lens 54 may act to reduce the reflection of emitted light as light leaves opto-electronic component 154, as compared to the amount of light reflected when opto-electronic component 154 is interfaced with air. Similarly, employing index matching material 168 to optically couple light receiving opto-electronic component 164 with lens 56 may act to reduce reflections of received light at lens 56 as compared to reflections that would otherwise occur when lens 56 is interfaced with air.

Employing index matching material 168 to reduce light reflections at the interface between the cavity of emit module 46 and lens 54 and the interface between lens 56 and the cavity of receive module 48 may generally increase the optical efficiency of the modules. Example materials and their respective index of refraction values that may be employed as index matching material 168 are disclosed in U.S. application Ser. No. 11/955,056, entitled "IMPLANTABLE OPTICAL SENSOR AND METHOD FOR MANUFACTURE," to Kuhn et al., filed Dec. 12, 2007 and published as U.S. Publication No. 2009/0156912 on Jun. 18, 2009, which is incorporated in its entirety herein by this reference. Index matching material 168 may substantially fill the cavity of each of emit and receive modules 46, 48 in which light emitting opto-electronic component 154 and light receiving opto-electronic component 164 are respectively arranged, as illustrated in FIG. 6B. In other examples, however, the cavity of one or both of emit and receive modules 46, 48 may be only partially filled with index matching material 168 or may be filled with multiple materials, at least one of which is an index matching material.

In order to detect changes in a physiological condition of patient 14, light emitting opto-electronic component 154 emits an optical signal through transparent lens 54 into adjacent body fluid or tissue volume 140. The optical signal from light emitting opto-electronic component 154 interacts with adjacent body fluid or tissue volume 140 of patient 14, after which a portion of the optical signal modulated by the body fluid or tissue volume of the patient is reflected off of the fluid or volume through lens 56 of receive module 48. In some examples, lens 56 may include a thin film or other coating that acts to filter light signals at colors and/or wavelengths of interest. The optical signal received by receive module 48 is detected by light receiving opto-electronic component 164. The modulation of the optical signal received by light receiving opto-electronic component 164 from light emitting opto-electronic component 154 may be interpreted by optical sensor module 87 and/or processor 80 of IMD 16 to detect a physiological condition of patient 14, e.g. to detect blood oxygen saturation or tissue perfusion of the patient, in response to which IMD 16 may, e.g., deliver electrical stimulation therapy or modify electrical stimulation therapy already being delivered via one or more of leads 18, 20, and 22 to heart 12 of patient 14 to restore normal hemodynamic function.

The examples described in this disclosure are directed to techniques for improving optical sensor signal amplitude for a target sensor sensitivity, i.e. for a target edge-to-edge lens spacing. In the examples disclosed, lens spacing is set to a value to achieve target sensor sensitivity, and other optical sensor parameters are varied in order to increase signal amplitude without increasing power demand. In some examples, the size, $D_E$ and $D_R$ of emit and receive lenses 54, 56 respectively, and the offset between each of lenses 54, 56, and emit and light emitting and receiving devices 154, 164, respectively, e.g. offset distance O shown in FIG. 6B, are selected to increase the amplitude of the signal that is received by light receiving opto-electronic component 164 of receive module 48 from light emitting opto-electronic component 154 of emit module 46.

With reference to the size of lenses 54, 56 of the example of FIGS. 6A and 6B, optical efficiency generally increases with decreasing lens diameter for constant edge-to-edge lens spacing, holding emit and receive lens diameters, $D_E$, $D_R$, respectively, equal, and coating circuit boards 150, 160 and side walls 152, 162 with a reflective material. The particular lens diameter selected for emit and receive lenses 54, 56 may be bounded by upper and lower limits. An upper limit may define, for example, a lens diameter above which optical efficiency is only nominally affected by the size of lenses 54, 56 in either or both of emit and receive modules 46, 48, respectively. In some examples, the diameter, $D_E$, of emit lens 54, and the diameter, $D_R$, of receive lens 56 may be less than approximately 6 millimeters (0.24 inches). In some examples, there may also be a lower limit on the diameter, $D_E$, of emit lens 54, or the diameter, $D_R$, of receive lens 56. For example, generally speaking, in order to best communicate the optical signal emitted by light emitting opto-electronic component 154 to body fluid or tissue volume 140, the diameter, $D_E$, of emit lens 54 should be greater than an area of the light signal emitted by light emitting opto-electronic component 154. In examples in which light emitting opto-electronic component 154 includes, e.g., an LED, the light signal generated by the LED is essentially a point source that radiates light out in all directions from a point on the component. In examples in which light emitting opto-electronic component 154 includes a VCSEL or other collimated light source, on the other hand, the light signal is generally in the form of a coherent beam. In one example, the diameter, $D_E$, of emit lens 54 may be greater than in a range from approximately 5 to approximately 10 times the area of the light signal emitted by light emitting opto-electronic component 154. The light emitting area of light emitting opto-electronic component may be, e.g., the area of the projected beam at the outer surface of lens 54.

Optical efficiency of emit and receive modules 46, 48 may be further improved by decreasing emit lens 54 diameter, $D_E$, while maintaining or increasing receive lens 56 diameter, $D_R$. Increasing optical efficiency by decreasing emit lens diameter may be caused by an increased concentration of light transmitted by light emitting opto-electronic component 154 through lens 54 to body fluid or tissue volume 140. However, decreasing receive lens 56 diameter, $D_R$, may act to decrease the total light received by light receiving opto-electronic component 164. Therefore, although, in some configurations where emit and receive lens diameters are equal, the impact of decreased reception may be overcome by the benefit of increased transmission, optical efficiency of emit and receive modules 46, 48 may be further improved by forming the emit module with emit lens 54 diameter, $D_E$, that is less than receive lens 56 diameter, $D_R$.

Although lens size has been described with reference to the diameter of disc shaped lenses 54 and 56 of the examples of FIGS. 2, 3 and 6, in other examples according to this disclosure the lenses employed in emit and receive modules of an optical sensor may have different shapes and their sizes may therefore be characterized by dimensions other than a diameter. In one example, instead of having the generally circular configuration of lenses 54 and 56, emit and/or receive modules of an optical sensor may have generally rectilinear lenses. In such examples, lens size may be characterized by, e.g., the length or the width of the lens.

Another parameter that may affect the optical efficiency of emit and receive modules 46, 48 is the offset O between one of light emitting and receiving devices 154, 164 and respective one of lenses 54, 56. Decreasing the opto-electronic component-lens offsets $O_E$ and $O_R$ of both emit and receive modules 46, 48, respectively, may generally act to increase optical efficiency. In some examples, the opto-electronic component-lens offsets $O_E$ and $O_R$ of both emit and receive modules 46, 48, respectively, may be selected based on the diameter of emit and receive lenses 54, 56, respectively.

As with lens diameter, the particular opto-electronic component-lens offsets $O_E$ and $O_R$ of emit and receive modules 46, 48, respectively, may be bounded by upper and lower limits. An upper limit may include, for example, an opto-electronic component-lens offset that is approximately equal to 1 times the diameter of the lens. For example, the distance that light emitting opto-electronic component 154 is offset from lens 54, i.e. $O_E$ shown in FIG. 6B, may be approximately equal to the diameter, $D_E$, of the emit lens. A lower limit on the opto-electronic component-lens offsets $O_E$ and $O_R$ for emit module 46 and receive module 48 may be approximately equal to zero such that the opto-electronic component abuts the module lens. For example, the distance that light emitting opto-electronic component 154 is offset from lens 54, i.e. $O_E$ shown in FIG. 6B, may be approximately equal to zero such that the light emitting opto-electronic component abuts the emit lens.

Figure 7A:
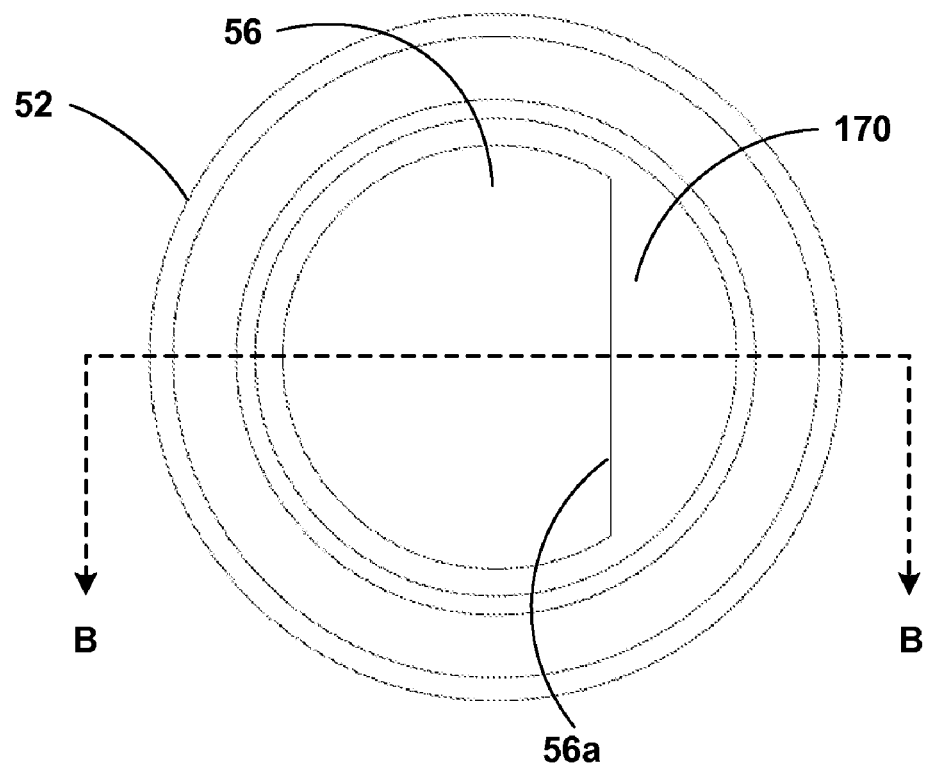
FIGS. 7A and 7B are plan and section views, respectively, of a ferrule of an optical sensor module including a flange masking the module lens.
Figure 7B:
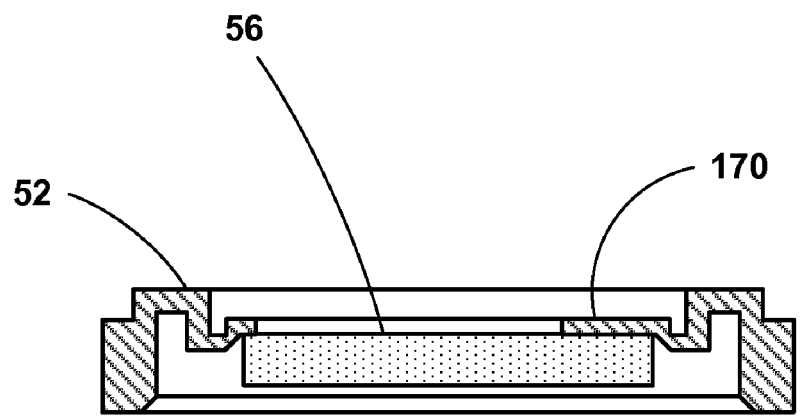

In addition to lens size and opto-electronic component-lens offset, in some examples, the arrangement of light receiving opto-electronic component 164 within receive module 48 and the effective spacing of lenses 54, 56 are improved by masking receive module lens 56 with flange 170 to create masked lens edge 56a that is aligned with light receiving opto-electronic component leading edge 164a and that acts to effectively increase the edge-to-edge lens spacing between emit and receive modules 46, 48. In the example of FIGS. 6A and 6B, flange 170 protrudes from ferrule 52 of receive module 48. FIGS. 7A and 7B are plan and section views, respectively, which illustrate in greater detail ferrule 52 including flange 170 masking lens 56. The section view of FIG. 7B is cut along section line B-B of FIG. 7A. Although the example of FIGS. 6A-7A illustrate flange 170 that creates a substantially linear masked lens edge 56a of lens 56, in other examples, the opaque member masking the lens of receive module 48 may be curved or otherwise contoured in a non-linear configuration.

As described above, generally speaking, sensor sensitivity may be controlled by varying the spacing between lenses 54, 56 of emit and receive modules 46, 48 respectively. Varying lens spacing, and, in particular, increasing lens spacing increases sensor sensitivity. However, as lens spacing is increased, the optical signal reaching light receiving opto-electronic component 164 decreases exponentially. The distribution of light over receive lens 56 also decreases exponentially with distance from the emit lens 54. Therefore, for a given lens edge-to-edge distance, the optimal position of light receiving opto-electronic component 164 is to be as close to the leading edge in the direction of light travel between emit module 46 and receive module 48 of receive lens 56 as possible.

Lens spacing may generally be defined by edge-to-edge spacing between lenses 54, 56, which is illustrated in FIG. 6A as $E_1$. Sensor lenses, including, e.g., lenses 54 and 56 of the example of FIGS. 6A and 6B, are commonly produced in a disc shape. Opto-electronic components, on the other hand, including, e.g., emitting and receiving opto-electronic components 154, 164 of the example of FIGS. 6A and 6B, are commonly produced in rectilinear shapes. As a result, rectilinear light emitting opto-electronic component 154 and light receiving opto-electronic component 164 cannot be arranged with their respective leading edges 154a, 164a in the direction of light travel from emit module 46 to receive module 48 aligned with the edges of disc shaped lenses 54 and 56 respectively.

The misalignment of opto-electronic leading edge and lens edge may have a greater performance impact on receive module 48 than emit module 46. In some examples according to this disclosure, therefore, flange 170 may be employed to mask lens 56 to create masked lens edge 56a that is aligned with light receiving opto-electronic component leading edge 164a. In examples employing flange 170 to mask lens 56, edge-to-edge lens spacing may be defined by $E_2$, instead of $E_1$. Therefore, masking lens 56 to create masked lens edge 56a aligned with light receiving opto-electronic component leading edge 164a also acts to effectively increase the edge-to-edge lens spacing between emit and receive modules 46, 48 by a distance A.

In some examples, lens 56 may be masked by a different opaque member than flange 170 protruding from ferrule 52 shown in the example of FIGS. 6A-7B. In one example, lens 56 may be masked by a flange protruding from another component of receive module 48 including, e.g., side wall 162. In another example, a separate component arranged, e.g. within the cavity of receive module 48 may be employed to mask lens 56. Additionally, in one example, lens 56 may be masked by an opaque film. As shown in FIGS. 6A and 6B, light emitting module 46 and light receiving module 48 may include transparent polymeric seals 156, 166, respectively, which may be formed over lenses 54, 56 and ferrules 50, 52, respectively. Seals 156, 166 may be formed, for example, from silicone rubber, polyurethane, or another optically transparent and biocompatible material. Seals 156, 166 may function to protect the joints between lenses 54, 56 and ferrules 50, 52 from the corrosive effects of bodily fluids and provide a smooth, convex surface that reduces the susceptibility of light emitting and receiving modules 46, 48 to blood clot formation and excessive tissue encapsulation over lenses 54, 56. In some examples, seals employed to cover one or both of lenses 54, 56 may include rougher surface textures, as well as shapes other than the convex shape of example seals 156, 166 shown in FIGS. 6A and 6B. In examples employing seals 156, 166, e.g. the example of FIGS. 6A and 6B, an opaque film, which may include a coating or an etched region, may be arranged over seal 166 to mask lens 56 arranged below seal 166. In another example, however, the opaque film may coat or be etched into the inner or outer surface of lens 56. Improving lens spacing and opto-electronic component placement may, in some examples, also be accomplished by, e.g., employing a rectilinear lens. However, such lens shapes may be less reliable and more expensive to manufacture and/or assemble.

In one example employing an opaque film to mask lens 56 of receive module 48, the film may include a coating of a refractory or non-refractory material applied to the inner surface or outer surface of the lens. Refractory materials may be employed, e.g., in examples in which the film that masks lens 56 is arranged on an outer surface of the lens or is applied over seal 166. Example materials that may be used for an opaque film to mask lens 56 of receive module 48 include niobium, refractory, and gold, non-refractory.

Housing 17 of IMD 16 may be formed, in some examples, from titanium, stainless steel, ceramic, glass, or a rigid polymer. In one example, housing 17 and ferrules 50, 52 are each formed from titanium and the ferrules are welded within openings formed in housing 17 to maintain hermeticity of light emitting and receiving modules 46, 48 and IMD 16. Lenses 54, 56 of light emitting and receiving modules 46, 48 respectively may be formed from, e.g., sapphire and are hermetically sealed in openings formed in housing 17 of IMD 16 using ferrules 50, 52, respectively. In some examples, lenses 54, 56 and ferrules 50, 52 may be bonded in a number of ways including using, e.g., gold braze joints or a polymer adhesive. The appropriate bond between lenses 54, 56 and ferrules 50, 52 may depend on the material from which the ferrules are formed and other manufacturing processes used in fabricating light emitting and receiving modules 46, 48.

As illustrated in example emit and receive modules 46, 48 of FIGS. 6A and 6B, inner surfaces 152a, 162a of sidewalls 152, 162 mate with respective outer surfaces 50a, 52a of ferrules 50, 52. In different examples of emit and receive modules 46, 48, inner surfaces 152a, 162a of sidewalls 152, 162 may be joined with respective outer surfaces 50a, 52a of ferrules 50, 52 in a variety of ways. In one example, side walls 152, 162 may be welded to ferrules 50, 52, respectively. In another example, side walls 152, 162 and respective ferrules 50, 52 may be joined with braze joints or an adhesive. In one example, side walls 152, 162 and respective ferrules 50, 52 may be sized such that inner surfaces 152a, 162a of the sidewalls form an interference fit with respective outer surfaces 50a, 52a of the ferrules.

In examples in which circuit boards 150, 160 are merged to include a single board that spans both emit and receive modules 46, 48, one side wall, e.g. 162 may be mated to one ferrule 52 with a relatively small dimensional tolerance, while the other side wall, e.g. side wall 152 is mated to the other ferrule 50a with a larger dimensional tolerance. Such an arrangement in which the dimensional tolerances of the respective joints between side walls 152, 162 and ferrules 50, 52 may act to allow tolerance stack-ups. To provide additional flexibility in the fabrication of emit and receive modules 46, 48, the joint between side wall and ferrule, e.g. side wall 152 and ferrule 50 may include a slot, e.g. in one of inner sidewall surface 152a or outer ferrule surface 50a to allow additional relief when assembly the components of the modules.

Figure 8:
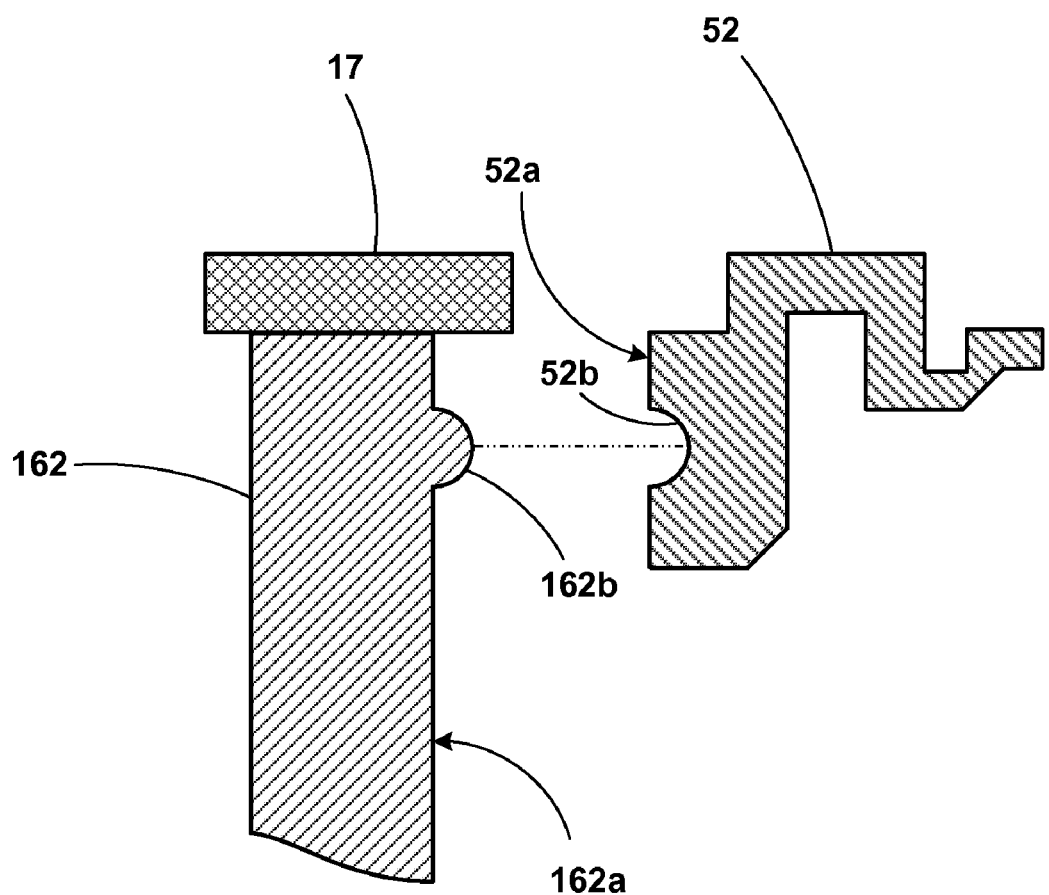
FIG. 8 is a partial section view of one module of the optical sensor of FIGS. 6A and 6B.

One example in which the inner surface of an optical sensor module side wall mates with the outer surface of a ferrule is illustrated in FIG. 8. FIG. 8 is a partial section view of receive module 48 of FIG. 6B illustrating in greater detail the junction between housing 17, side wall 162, and ferrule 52. To more clearly illustrate the features of the example of FIG. 8, ferrule 52 has been exploded away from side wall 162 and housing 17. In FIG. 8, inner surface 162a of side wall 162 includes protrusion 162b received by concavity 52b in outer surface 52a of ferrule 52. Protrusion 162b may, in some examples, include a number of protrusions distributed around inner surface 162a of side wall 162. In examples in which protrusion 162b includes a number of protrusions distributed around inner surface 162a of side wall 162, concavity 52b may include a corresponding number of dimples distributed around outer surface 52a of ferrule 52 such that each protrusion in the inner surface of the side wall is received by a respective one of the dimples in the outer surface of the ferrule. In other examples, however, protrusion 162b may be formed as a substantially continuous rib around all or most of inner surface 162a of side wall 162, in which case, concavity 52b may be formed as a corresponding continuous channel in outer surface 52a of ferrule 52 to receive the rib protruding from the inner surface of the side wall.

Although protrusion 162b and concavity 52b in side wall 162 and ferrule 52 respectively are illustrated in the example of FIG. 8 as formed in a generally arcuate shape, in other examples, the side wall protrusion and corresponding ferrule concavity may have other shapes including, e.g., a generally rectilinear shape. Additionally, although inner surface 162a of side wall 162 is shown as including protrusion 162b and outer surface 52a of ferrule 52 is shown as including concavity 52b in the example of FIG. 8, in other examples, the inner surface of the side wall my include a concavity that is configured to receive a protrusion in the outer surface of the ferrule.

Figure 9:
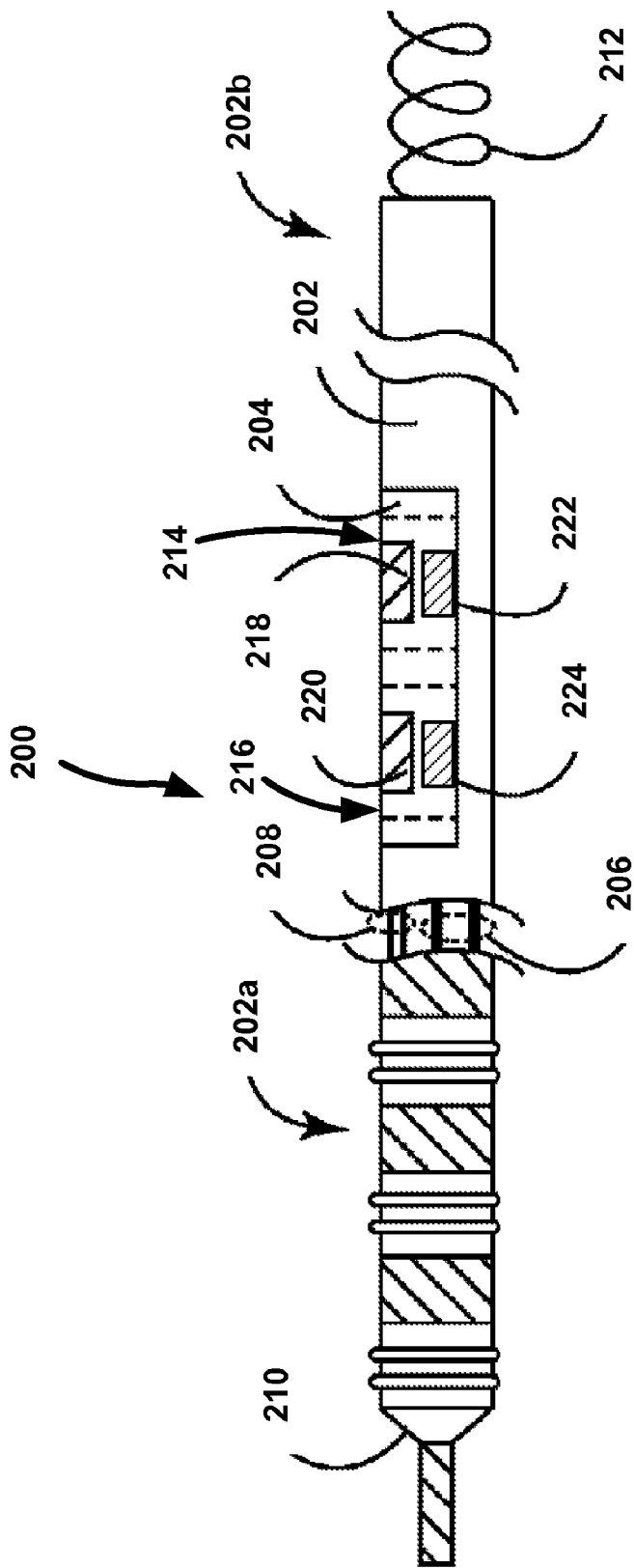
FIG. 9 is a conceptual drawing illustrating an example medical lead including an optical sensor.

Although the foregoing examples have been described with reference to an optical sensor employed in IMD 16, optical sensors according to this disclosure may also be employed in other types of implantable devices. For example, FIG. 9 is a conceptual drawing illustrating example medical lead 200 including body 202, optical sensor 204, conductors 206 and 208, connector assembly 210, and fixation member 212. Lead 200 includes elongated body 202 extending between proximal end 202a and distal end 202b. Optical sensor 204 is positioned along lead body 202, in some examples, near distal end 202b of the lead body. Sensor 204 includes at least two modules, e.g. emit module 214 and receive module 216, which modules respectively include windows 218 and 220 through which emitted light and scattered light travels from/to light emitting opto-electronic component 222 and light receiving opto-electronic component 224, respectively, of sensor 204.

Lead body 202 carries separately insulated conductor pairs 206 and 208 between proximal connector assembly 210 and sensor 204. Conductor pair 206 is provided for carrying drive signals from proximal connector assembly 210 to light emitting opto-electronic component 218 via integrated circuitry in emit module 214. Conductor pair 208 is provided for carrying current generated by light receiving opto-electronic component 224 included in receive module 216 to proximal connector assembly 210. Connector assembly 210 may be coupled to an implantable medical device to thereby couple optical sensor 204 to a sensor module included in the medical device, e.g. optical sensor module 87 of IMD 16 shown in FIG. 3. The sensor module may include sensor driver circuitry and signal processing circuitry (not shown in FIG. 9).

Lead 200 is shown having a distal fixation member 212 for anchoring the position of distal end 202b of lead body 202 at a targeted implant location, e.g. within patient 14. In some examples, fixation member 212 may serve as an electrode and be coupled to an insulated conductor extending to proximal connector assembly 210. Additionally, in some examples lead 200 may include other sensors and/or electrodes including, e.g. electrical stimulation electrodes. As such, it is recognized that the particular configurations of lead body 202, conductors carried by the lead body and proximal connector assembly 210 will depend on the particular configuration of electrodes and sensors carried by lead 200. In some examples, lead 200 may also include an open lumen, for example for use in delivering a fluid agent or passing a guide wire.

Figure 10:
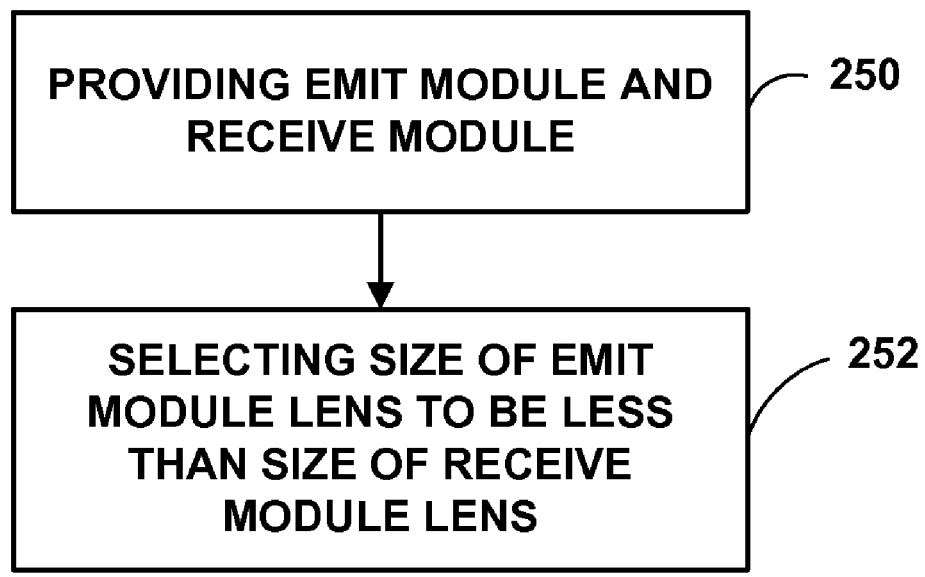
FIGS. 10-12 are flow diagrams illustrating several example methods of constructing an optical sensor according to this disclosure connected to a housing of an IMD.
Figure 11:
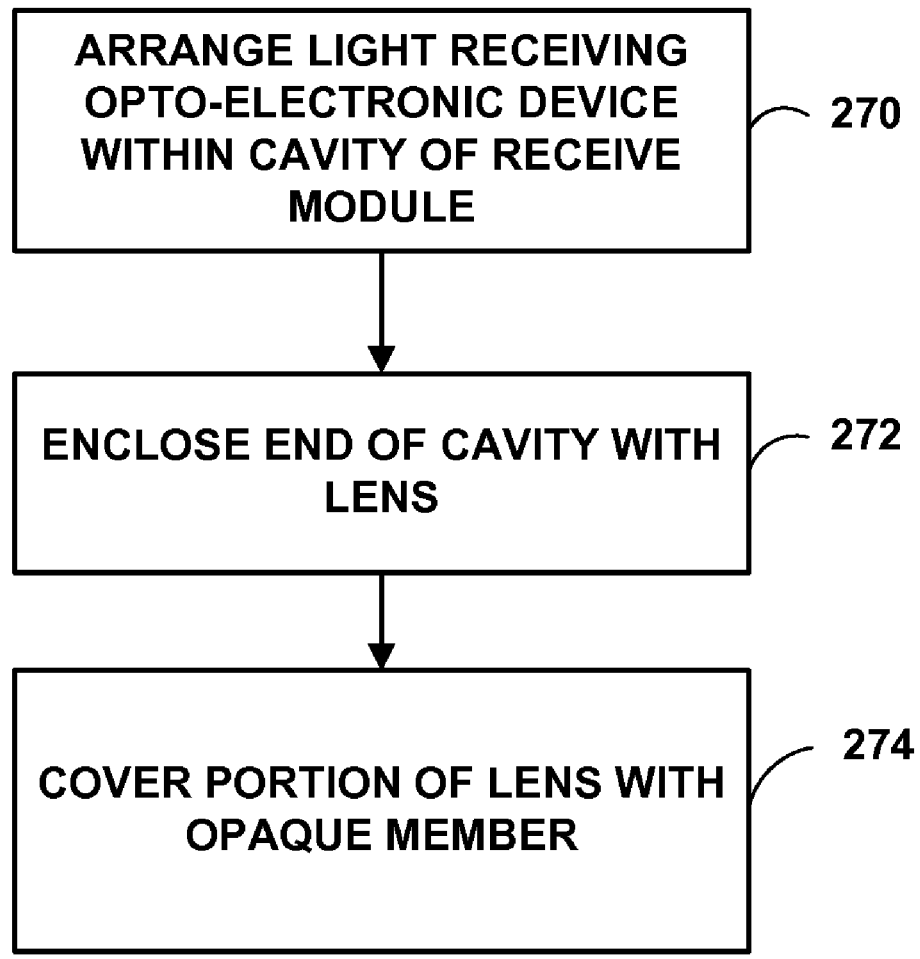
Figure 12:
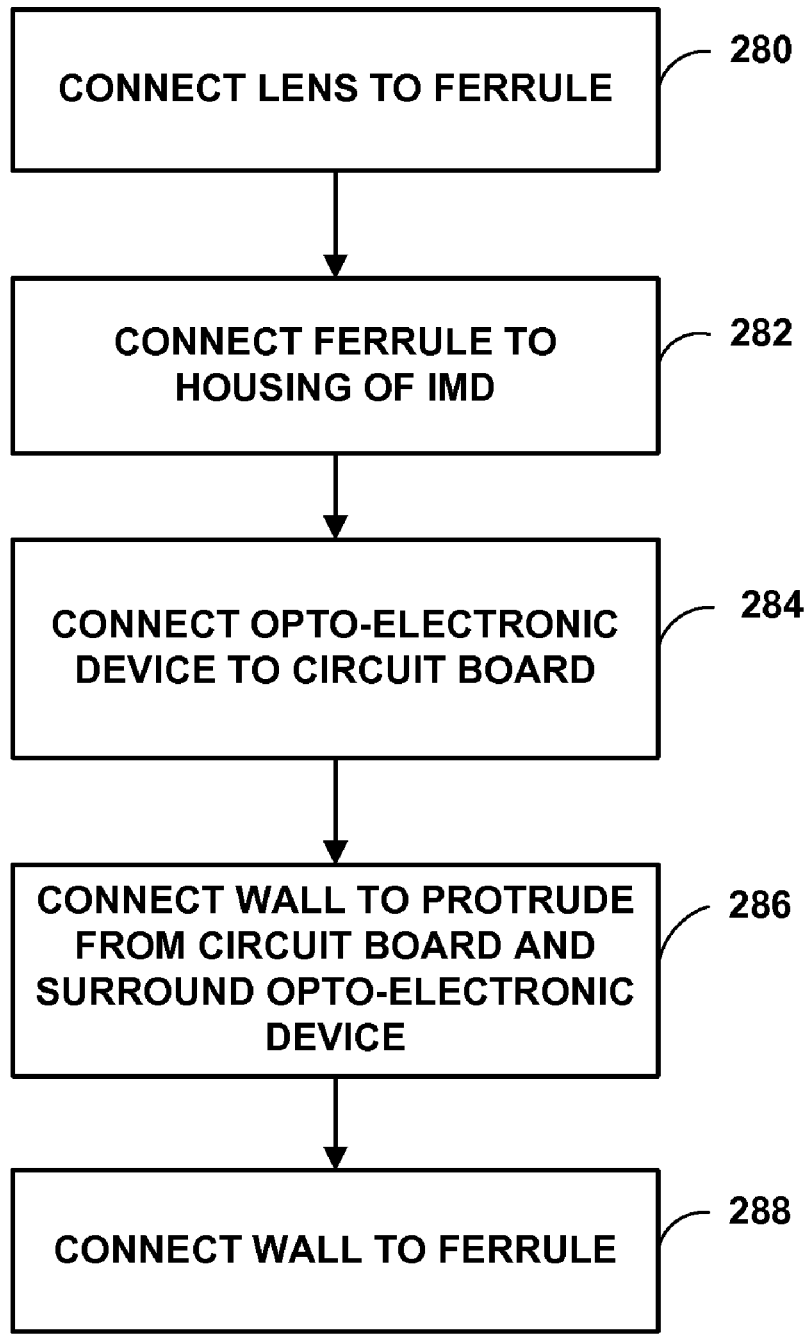

FIGS. 10-12 are flow diagrams illustrating several example methods of constructing an optical sensor according to this disclosure connected to a housing of an IMD. The methods of FIGS. 10-12 will be described with reference to the example sensor of FIGS. 6A and 6B connected to housing 17 of IMD. However, the methods may be applied to optical sensors connected to other medical devices including, e.g., lead 200 of FIG. 9.

FIG. 10 is a flow diagram of an example method of constructing an example of optical sensor 42 of FIGS. 6A and 6B. The method of FIG. 10 includes providing emit module 46 and receive module 48 offset laterally from the emit module (250). In the example of FIG. 10, each of emit and receive modules 46, 48 includes a cavity within which one of light emitting opto-electronic component 154 or light receiving opto-electronic component 164 is arranged. One of emit or receive lenses 54, 56 generally defines one end of the cavity offset from the one of light emitting opto-electronic component 154 or light receiving opto-electronic component 164. The method of FIG. 10 also includes selecting a size of lens 54 of emit module 46 to be less than a size of lens 56 of receive module 48 (252).

FIG. 11 is a flow diagram of another example method of constructing another example of optical sensor 42 of FIGS. 6A and 6B. Light receiving opto-electronic component 164 including first edge 164a is arranged within a cavity of receive module 48 (270). One end of the cavity of receive module 48 offset from light receiving opto-electronic component 164 is enclosed with lens 56 (272) and a portion of lens 56 is covered with an opaque member including, e.g. flange 170 to form masked lens edge 56a substantially aligned with first edge 164a of light receiving opto-electronic component 164 (274).

FIG. 12 is a flow diagram of another example method of constructing another example of optical sensor 42 of FIGS. 6A and 6B. For convenience, the method of FIG. 12 is described with reference to the construction of emit module 46. However, the method may also be applied to the construction of receive module 48. The method of FIG. 12 includes connecting lens 56 to ferrule 50 (280), e.g., by brazing the lens to the ferrule. Ferrule 50 is connected to housing 17 of IMD 16 (282), e.g., by welding the ferrule to the housing. Light emitting opto-electronic component 154 is mounted on a surface of circuit board 150 (284). Wall 152 is connected to circuit board 150 to protrude from the surface of the circuit board and surround light emitting opto-electronic component 154 (286). Finally, wall 152 is connected to ferrule 50 such that inner surface 152a of the wall mates with outer surface 50a of the ferrule (288).

The techniques disclosed herein may provide several advantages for optical sensors employed in implantable medical devices. In particular, the examples described in this disclosure are directed to techniques for improving optical sensor signal amplitude for a target sensor sensitivity without increasing power demand. In some examples, sensor signal amplitude is increased by decreasing lens size and/or an offset between opto-electronic component and lens for one or both of an emit module and receive module of an optical sensor. Additionally, in some examples, the arrangement of the opto-electronic component within the receive module is improved by masking the receive module lens with an opaque member to create a masked lens leading edge that is aligned with a leading edge of the opto-electronic component and that acts to effectively increase the edge-to-edge lens spacing between the emit and receive modules.

Various examples have been described. These and other examples are within the scope of the invention defined by the following claims.

The invention claimed is:

1. A medical device comprising:
a housing; and
an optical sensor connected to the housing and comprising:
    an emit module; and
    a receive module offset laterally from the emit module, wherein each of the emit and receive modules comprises
        a cavity within which an opto-electronic component is arranged and a lens generally defining one end of the cavity offset from the opto-electronic component,
        wherein a size of the lens of the emit module is less than a size of the receive module, and wherein at least one of the emit module or the receive module comprises:
a wall surrounding the opto-electronic component;
a circuit board offset from the lens and to which the opto-electronic component and the wall are connected to define another end of the cavity; and
a ferrule connected to the housing, the wall, and the lens.

2. The device of claim 1, wherein the emit module opto-electronic component comprises at least one of a light emitting diode or a vertical cavity surface emitting laser.

3. The device of claim 1, wherein the receive module opto-electronic component comprises at least one of a photoresistor, a light dependent resistor, a photodiode, a phototransistor, a photovoltaic cell, a light emitting diode or a charge-coupled device.

4. The device of claim 1, wherein the cavity of each of the emit and receive modules is further defined by a wall surrounding the opto-electronic component arranged within the cavity and a circuit board offset from the lens and to which the opto-electronic component is connected, and wherein an inner surface of the wall and a surface of the circuit board to which the opto-electronic component is connected each comprise a reflective material.

5. The device of claim 1, wherein the cavity of at least one of the emit module or the receive module is at least partially filled with an index matching material.

6. The device of claim 1, wherein an inner surface of the wall mates with an outer surface of the ferrule.

7. The device of claim 1 further comprising a transparent seal arranged over an outer surface of the lens of at least one of the emit module or the receive module.

8. The device of claim 7, wherein the seal comprises a biocompatible polymeric material.

9. The device of claim 7, wherein the seal comprises at least one of silicone or polyurethane.

10. The device of claim 1, wherein the medical device comprises at least one of a pulse generator or a medical lead.

11. The device of claim 1, wherein the optical sensor comprises at least one of a blood oxygen saturation, a blood glucose level, or a tissue perfusion sensor.

12. The device of claim 1, wherein the lens is offset from the opto-electronic component by a distance based on a major dimension of the lens.

13. The device of claim 12, wherein the distance the lens is offset from the opto-electronic component is in a range from approximately 0 to approximately 1 times the major dimension of the lens.

14. The device of claim 12, wherein the lens comprises a generally disc shaped lens, and wherein the major dimension is a diameter of the disc shaped lens.

15. The device of claim 1 further comprising an opaque member partially covering the lens to form a masked lens edge substantially aligned with a first edge of the opto-electronic component.

16. An optical sensor connected to a housing of a medical device, the sensor comprising:
an emit module; and
a receive module offset laterally from the emit module,
wherein each of the emit and receive modules comprises a cavity within which an opto-electronic component is arranged and a lens generally defining one end of the cavity offset from the opto-electronic component,
wherein a size of the lens of the emit module is less than a size of the lens of the receive module, and
wherein at least one of the emit module or the receive module comprises:
a wall surrounding the opto-electronic component;
a circuit board offset from the lens and to which the opto-electronic component and the wall are connected to define another end of the cavity; and
a ferrule connected to the housing, the wall, and the lens.

17. The sensor of claim 16, wherein the emit module opto-electronic component comprises at least one of a light emitting diode or a vertical cavity surface emitting laser.

18. The sensor of claim 16, wherein the receive module opto-electronic component comprises at least one of a photoresistor, a light dependent resistor, a photodiode, a phototransistor, a photovoltaic cell, or a charge-coupled device.

19. The sensor of claim 16, wherein the cavity of each of the emit and receive modules is further defined by a wall surrounding the opto-electronic component arranged within the cavity and a circuit board offset from the lens and to which the opto-electronic component is connected, and wherein an inner surface of the wall and a surface of the circuit board to which the opto-electronic component is connected each comprise a reflective material.

20. The sensor of claim 16, wherein the cavity of at least one of the emit module or the receive module is at least partially filled with an index matching material.

21. The sensor of claim 16, wherein an inner surface of the wall mates with an outer surface of the ferrule.

22. The sensor of claim 16 further comprising a transparent seal arranged over an outer surface of the lens of at least one of the emit module or the receive module.

23. The sensor of claim 22, wherein the seal comprises a biocompatible polymeric material.

24. The sensor of claim 22, wherein the seal comprises at least one of silicone or polyurethane.

25. The sensor of claim 16, wherein the medical device comprises at least one of a pulse generator or a medical lead.

26. The sensor of claim 16 configured to sense at least one of blood oxygen saturation level, blood glucose level, or tissue perfusion sensor.

27. The sensor of claim 16, wherein the lens is offset from the opto-electronic component by a distance based on a major dimension of the lens.

28. The sensor of claim 27, wherein the distance the lens is offset from the opto-electronic component is in a range from approximately 0 to approximately 1 times the major dimension of the lens.

29. The sensor of claim 27, wherein the lens comprises a generally disc shaped lens, and wherein the major dimension is a diameter of the disc shaped lens.

30. A method of constructing an optical sensor connected to a housing of a medical device, the method comprising:
providing an emit module and a receive module offset laterally from the emit module, wherein each of the emit and receive modules comprises a cavity within which an opto-electronic component is arranged and a lens generally defining one end of the cavity offset from the opto-electronic component, and at least one of the emit module or the receive module comprises a wall surrounding the opto-electronic component, a circuit board offset from the lens and to which the opto-electronic component and the wall are connected to define another end of the cavity, and a ferrule connected to the housing, the wall, and the lens; and
selecting a size of the lens of the emit module to be less than a size of the lens of the receive module.

* * * * *